US009233887B2

(12) United States Patent
Dakka et al.

(10) Patent No.: US 9,233,887 B2
(45) Date of Patent: Jan. 12, 2016

(54) PROCESS FOR PRODUCING A MONOCYCLOALKYL-SUBSTITUTED AROMATIC COMPOUND

(75) Inventors: Jihad M. Dakka, Whitehouse Station, NJ (US); Teng Xu, Houston, TX (US); Edward A. Lemon, Mickleton, NJ (US); James R. Lattner, LaPorte, TX (US); Jane C. Cheng, Bridgewater, NJ (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 13/885,611

(22) PCT Filed: Nov. 4, 2011

(86) PCT No.: PCT/US2011/059317
§ 371 (c)(1),
(2), (4) Date: Aug. 16, 2013

(87) PCT Pub. No.: WO2012/087433
PCT Pub. Date: Jun. 28, 2012

(65) Prior Publication Data
US 2014/0336422 A1    Nov. 13, 2014

Related U.S. Application Data

(60) Provisional application No. 61/425,421, filed on Dec. 21, 2010.

(30) Foreign Application Priority Data

Feb. 8, 2011    (EP) .................................... 11153690

(51) Int. Cl.
| | | |
|---|---|---|
| *C07C 2/66* | (2006.01) | |
| *C07C 37/07* | (2006.01) | |
| *C07C 37/08* | (2006.01) | |
| *C07C 45/53* | (2006.01) | |

(52) U.S. Cl.
CPC . *C07C 2/66* (2013.01); *C07C 37/07* (2013.01); *C07C 37/08* (2013.01); *C07C 45/53* (2013.01); *C07C 2529/08* (2013.01); *C07C 2529/18* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 3,197,399 A | 7/1965 | Wight et al. | |
| 3,201,356 A | 8/1965 | Kress et al. | |
| 3,347,945 A | 10/1967 | Slaugh | |
| 3,390,101 A | 6/1968 | Csicsery | |
| 3,412,165 A | 11/1968 | Slaugh et al. | |
| 3,760,017 A | 9/1973 | Arkell et al. | |
| 3,760,018 A | 9/1973 | Suggitt et al. | |
| 3,760,019 A | 9/1973 | Crone, Jr. et al. | |
| 3,784,617 A | 1/1974 | Suggitt et al. | |
| 3,784,618 A | 1/1974 | Suggitt et al. | |
| 3,786,106 A * | 1/1974 | Zuech et al. | ............... 585/427 |
| 3,839,477 A | 10/1974 | Suggitt et al. | |
| 3,864,421 A | 2/1975 | Suggitt | |
| 3,957,687 A | 5/1976 | Arkell et al. | |
| 4,021,490 A | 5/1977 | Hudson | |
| 4,094,918 A | 6/1978 | Murtha et al. | |
| 4,122,125 A | 10/1978 | Murtha et al. | |
| 4,152,362 A | 5/1979 | Murtha | |
| 4,177,165 A | 12/1979 | Murtha et al. | |
| 4,206,082 A | 6/1980 | Murtha et al. | |
| 4,219,687 A | 8/1980 | Dolhyj et al. | |
| 4,219,689 A | 8/1980 | Murtha | |
| 4,268,699 A | 5/1981 | Murtha et al. | |
| 4,329,531 A | 5/1982 | Murtha et al. | |
| 4,380,683 A | 4/1983 | Dolhyj et al. | |
| 4,439,409 A | 3/1984 | Puppe et al. | |
| 4,447,554 A | 5/1984 | Murtha et al. | |
| 4,463,207 A * | 7/1984 | Johnson | ............... 585/462 |
| 4,826,667 A | 5/1989 | Zones et al. | |
| 4,870,217 A | 9/1989 | Knifton | |
| 4,954,325 A | 9/1990 | Rubin et al. | |
| 4,962,250 A | 10/1990 | Dessau et al. | |
| 5,037,538 A | 8/1991 | Chin et al. | |
| 5,053,571 A | 10/1991 | Makkee | |
| 5,108,969 A | 4/1992 | Del Rossi et al. | |
| 5,118,896 A | 6/1992 | Steigelmann et al. | |
| 5,146,024 A | 9/1992 | Reed | |
| 5,236,575 A | 8/1993 | Bennett et al. | |
| 5,250,277 A | 10/1993 | Kresge et al. | |

(Continued)

FOREIGN PATENT DOCUMENTS

| | | |
|---|---|---|
| EP | 0 293 032 | 11/1988 |
| EP | 0 338 734 | 10/1989 |

(Continued)

OTHER PUBLICATIONS

Kim et al., "Structural Evolution of B-MCM-36 and B-ITQ-2 from B-MCM-22", Bull, Korean Chem. Soc. 2006, vol. 27, No. 10, pp. 1693-1696.

Lawton et al., "Zeolite MCM-49; A Three-Dimensional MCM-22 Analogue Synthesized by in Situ Crystallization", J. Phys. Chem. 1996, 100, pp. 3788-3798.

Zhicheng et al., "Static synthesis of high-quality MCM-22 zeolite with high $SiO_2/Al_2O_3$ ratio", Chinese Science Bulletin 2004, vol. 49 No. 6, pp. 556-561.

Slaugh et al., "Hydrodimerization of Benzene to Phenylcyclohexane over Supported Transition Metal Catalysts", Journal of Catalysis 13, 1969, pp. 385-396.

(Continued)

*Primary Examiner* — Brian J Davis
(74) *Attorney, Agent, or Firm* — Siwen Chen; Stephen A. Baehl

(57) ABSTRACT

In a process for producing mono-cycloalkyl-substituted aromatic compound, benzene and cyclic monoolefin are contacted with a catalyst under alkylation conditions to produce an effluent containing mono-cycloalkyl-substituted aromatic compound. The catalyst comprises a molecular sieve.

11 Claims, 1 Drawing Sheet

(56) References Cited

U.S. PATENT DOCUMENTS

| | | | |
|---|---|---|---|
| 5,292,976 | A | 3/1994 | Dessau et al. |
| 5,362,697 | A | 11/1994 | Fung et al. |
| 5,384,296 | A | 1/1995 | Tsao |
| 5,554,274 | A | 9/1996 | Degnan et al. |
| 5,705,729 | A | 1/1998 | Huang |
| 6,037,513 | A | 3/2000 | Chang et al. |
| 6,049,018 | A | 4/2000 | Calabro et al. |
| 6,133,470 | A | 10/2000 | Beck et al. |
| 6,489,529 | B1 | 12/2002 | Cheng et al. |
| 6,506,953 | B1 | 1/2003 | Cheng et al. |
| 6,720,462 | B2 | 4/2004 | Duda et al. |
| 6,730,625 | B1 | 5/2004 | Chang et al. |
| 6,756,030 | B1 | 6/2004 | Rohde et al. |

FOREIGN PATENT DOCUMENTS

| | | | |
|---|---|---|---|
| EP | 0 387 080 | 9/1990 | |
| JP | 2005/342644 | 12/2005 | |
| WO | WO95/31421 | 11/1995 | |
| WO | WO97/17290 | 5/1997 | |
| WO | WO01/53236 | 7/2001 | |
| WO | WO01/74767 | 10/2001 | |
| WO | WO2005/118476 | 12/2005 | |
| WO | WO 2009/021604 | 2/2009 | |
| WO | WO 2009/021604 A1 * | 2/2009 | ............... C07C 2/74 |
| WO | WO 2009/038900 | 3/2009 | |
| WO | WO 2009/134516 | 11/2009 | |
| WO | WO 2009/134516 A1 * | 11/2009 | ............... C07C 2/74 |
| WO | WO 2010/098798 | 9/2010 | |
| WO | WO 2011/001244 | 1/2011 | |

OTHER PUBLICATIONS

Ruan et al. "*Structure Elucidation of the Highly Active Titanosilicate Catalyst Ti-YNU-1*", Angewandte Chemie, 2005, pp. 6719-6723.

Fan et al., "*Synthesis and catalytic properties of a new titanosilicate molecular sieve with the structure analogous to MWW-type lamellar precursor*", Journal of Catalysis 243, 2006, pp. 183-191.

Borodina et al., "*Hydroalkylation of benzene and ethylbenzene over metal containing zeolite catalysts*", Microporous and Mesoporous Materials 105, 2007, pp. 181-188.

Maheshwari et al., "*Layer Structure Preservation during Swelling, Pillaring, and Exfoliation of a Zeolite Precursor*", JACS Articles, 2008, pp. 1507-1516.

Wu et al., "*Methodology for Synthesizing Crystalline Metal-losilicates with Expanded Pore Windows Through Molecular Alkoxysilylation of Zeolitic Lamellar Precursors*", JACS Articles, 2008, pp. 8178-8187.

* cited by examiner

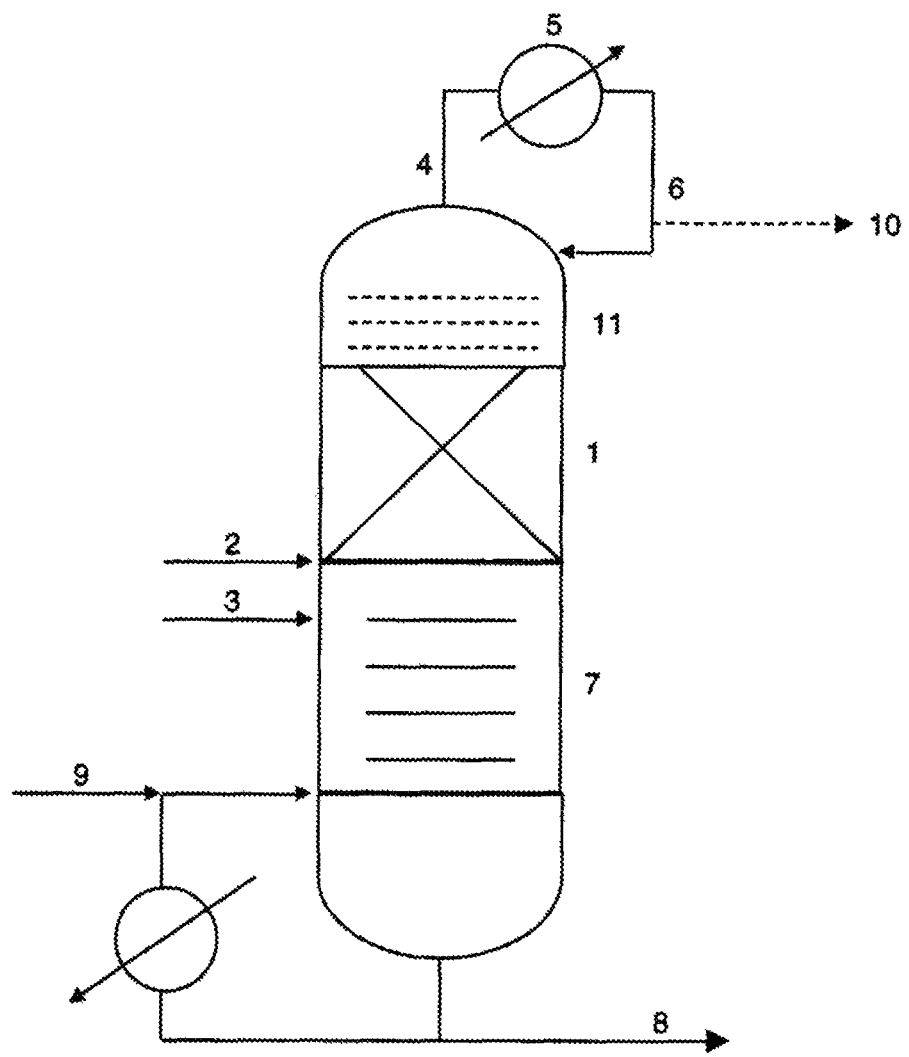

PROCESS FOR PRODUCING A MONOCYCLOALKYL-SUBSTITUTED AROMATIC COMPOUND

PRIORITY CLAIM TO RELATED APPLICATIONS

This application is a National Stage Application of International Application No. PCT/US2011/059317 filed Nov. 4, 2011, which claims priority to U.S. Provisional Application Ser. No. 61/425,421 filed Dec. 21, 2010, and European Patent Application No. 11153690.0 filed Feb. 8, 2011, both of which are incorporated herein by reference in their entirety.

FIELD OF THE INVENTION

The present invention relates to a process for producing a mono-cycloalkyl-substituted aromatic compound such as cyclohexylbenzene.

BACKGROUND

Phenol is an important product in the chemical industry and is useful in, for example, the production of phenolic resins, bisphenol A, $\epsilon$-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions and in the production of adipic acid, cyclohexanone resins, cyclohexanone oxime, caprolactam and nylon 6.

It is known from U.S. Pat. No. 5,053,571 that cyclohexylbenzene can be produced by contacting benzene with hydrogen in the presence of a catalyst comprising ruthenium and nickel supported on zeolite beta and that the resultant cyclohexylbenzene can be processed in two steps to cyclohexanone and phenol. The alkylation reaction is carried out at a liquid hourly space velocity (LHSV) ranging from 1 to 100, a reaction pressure ranging from 100 to 1000 kPa, a hydrogen feed rate ranging from 0.2 to 6 mole per mole of feedstock per hour, and a reaction temperature ranging from 100 to 300° C.

In addition, U.S. Pat. No. 5,146,024 discloses that benzene can be reacted with hydrogen in the presence of carbon monoxide and a palladium-containing zeolite X or Y to produce cyclohexylbenzene, which can then be converted in high yield to phenol and cyclohexanone by autooxidation with subsequent acid treatment. The alkylation reaction is carried out at a liquid hourly space velocity (LHSV) of the benzene feed of about 1 to about 100 hr$^{-1}$, a total reaction pressure of about 345 to about 10,350 kPa, a molar ratio of H$_2$ to benzene of about 0.1:1 to about 10:1, a molar ratio of carbon monoxide to H$_2$ of about 0.01:1 to about 0.3:1, and a temperature of about 100 to about 250° C.

Further, U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The catalyst may also contain a binder and/or matrix and in the Examples the catalyst is produced by impregnating an extrudate of the MCM-22 family molecular sieve and an alumina binder with an aqueous solution of a salt of the hydrogenation metal using incipient wetness impregnation. The '513 patent also discloses that the resultant cyclohexylbenzene can be oxidized to the corresponding hydroperoxide and the peroxide decomposed to the desired phenol and cyclohexanone.

According to the present invention, it has now been found that the benzene may be alkylated with a cyclic monoolefin using an alkylation catalyst comprising a molecular sieve to produce a mono-cycloalkyl-substituted aromatic compound.

SUMMARY

In one aspect, the invention resides in a process for producing a mono-cycloalkyl-substituted aromatic compound, the process comprising contacting benzene and cyclic monoolefin with a catalyst under alkylation conditions to produce an effluent containing mono-cycloalkyl-substituted aromatic compound and the catalyst comprising a molecular sieve.

Conveniently, the alkylation catalyst may comprise a composite comprising a molecular sieve and an inorganic oxide different from the molecular sieve.

Conveniently, the molecular sieve has an average pore size of at least $7 \times 10^{-10}$ m (7 Angstrom) and typically is selected from zeolite beta, faujasite, mordenite and a molecular sieve of the MCM-22 family.

Conveniently, the molecular sieve is an aluminosilicate and the molar ratio of the silica to the aluminum in the molecular sieve is in the range of 2:1 to 200:1, preferably in the range of 5:1 to 100:1, and more preferably in the range from 10:1 to 50:1.

Conveniently, the alkylation conditions include comprise a temperature of from 100° C. to 145° C., a pressure of from 345 kPag to 2068 kPag (50 psig to 300 psig), a cyclic monoolefin to benzene molar ratio of from 0.10:1 to 10:1.

Conveniently, the mono-cycloalkyl-substituted aromatic compound is cyclohexylbenzene and the cyclic monoolefin is cyclohexene.

In another aspect, the invention resides in a method for coproducing phenol and cyclohexanone, the method comprising producing cyclohexylbenzene by the process described herein, oxidizing the cyclohexylbenzene to produce cyclohexylbenzene hydroperoxide and cleaving the cyclohexylbenzene hydroperoxide to produce phenol and cyclohexanone. In a further embodiment, the cyclohexanone may be dehydrogenated to produce further phenol.

In still another aspect, the invention resides in a method for the catalytic distillation of a cyclic monoolefin and benzene wherein the cyclic monoolefin and benzene are alkylated to produce a mono-cycloalkyl-substituted aromatic compound.

Conveniently, the process for the production of mono-cycloalkyl-substituted aromatic compound comprises (a) feeding a cyclic monoolefin and benzene to a distillation column reactor comprising an alkylation catalyst wherein molar ratio the cyclic monoolefin to the benzene is from 0.01:1 to 100:1; (b) reacting at least a portion of the benzene with at least a portion of the cyclic monoolefin to form a reaction mixture comprising cyclohexylbenzene, benzene, and cyclic monoolefin; (c) separating the benzene from the mono-cycloalkyl-substituted aromatic compound; and (d) removing the cyclohexylbenzene from the distillation column reactor as bottoms.

BRIEF DESCRIPTION OF THE DRAWINGS

FIG. 1 illustrates a process for producing a mono-cycloalkyl-substituted aromatic compound using a catalytic distillation tower.

DETAILED DESCRIPTION OF THE EMBODIMENTS

Described herein is a process for the alkylation of benzene and cyclic monoolefin (e.g. cyclohexene) to produce a mono-cycloalkyl-substituted aromatic compound (e.g. cyclohexylbenzene). Insofar as the alkylation process produces di-cycloalkyl-substituted aromatic compound (e.g. dicyclohexylbenzene) in addition to the desired mono-cycloalkyl-substituted aromatic compound product, the process can include the further step of transalkylating the di-cycloalkyl-substituted aromatic compound with additional benzene to produce additional mono-cycloalkyl-substituted aromatic compound product.

Benzene Alkylation

Any commercially available benzene feed can be used in the alkylation step, but preferably the benzene has a purity level of at least 99 wt %. Conveniently, the total benzene feed to the alkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Any commercially available cyclic monoolefin feed (e.g. cyclohexene) can be used in the alkylation step, but preferably the cyclic monoolefin has a purity level of at least 99 wt %. Conveniently, the total cyclic monoolefin feed to the alkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The cyclic monoolefin may be produced by the hydrogenation of an aromatic compound. Preferably, the cyclic monoolefin is produced in an on-site hydrogenation reactor wherein the hydrogenation reactor is fed with benzene and hydrogen to produce cyclohexene. It would be preferable to use the same benzene feed for the hydrogenation step that is being made available to the alkylation reactor. Hydrogen can be supplied to the hydrogenation step over a wide range of values, but typically is arranged such that the molar ratio of hydrogen to benzene in the hydrogenation feed is between about 0.01:1 and about 100:1, such as between about 0.1:1 and about 10:1, for example between about 0.5:1 and about 1:1. In an alternative embodiment, the cyclic monoolefin can be produced by any method such as the dehydrogenation of an alicyclic such as cyclohexane.

The hydrogenation reaction may be conducted in the presence of a catalyst comprising at least one hydrogenation metal wherein the hydrogenation metal may be selected from any hydrogenation metal. Preferably the hydrogenation metal will be supported on any conventional catalyst support wherein the hydrogenation metal may be selected from palladium, ruthenium, nickel, cobalt and mixtures thereof.

In one embodiment, the operating temperature of the hydrogenation step is from 50° C. to 400° C. Preferably, the operating temperature of the hydrogenation process is from 50° C. to 350° C.; from 75° C. to 300° C.; from 100° C. to 250° C., from 100° C. to 200° C., and from 100° C. to 175° C., from 100° C. to 150° C., from 100° C. to 140° C., and from 100° C. to 125° C. In other embodiments, the operating temperature lower limit may be 50° C., 75° C., 100° C., 110° C., 120° C., 125° C., 130° C., 135° C., 140° C., 145° C.; and the upper limit temperature may be 500° C., 400° C., 300° C., 200° C., 190° C., 180° C., 170° C., 160° C., 150° C., 145° C., 140° C., 135° C., and 130° C. with ranges from any lower limit to any upper limit being contemplated.

In one embodiment, the hydrogenation reaction may have a partial conversion of the aromatic compound to the cyclic monoolefin such as a conversion of from about 1 wt % to about 99 wt %. In other embodiments, the aromatic compound conversion in the hydrogenation reactor is from 5 to 75 wt %, from 5 to 50 wt %, from 5 to 40 wt %, from 5 to 30 wt %, and from 5 to 20 wt %.

In one embodiment, the aromatic compound conversion in the hydrogenation step is from 1 wt % to 99.9 wt %. Preferably, the aromatic compound conversion of the hydrogenation step is from 5 to 95 wt %; from 5 to 95 wt %; from 5 to 85 wt %, from 5 to 75 wt %, and from 5 to 65 wt %, from 5 to 60 wt %, from 5 to 55 wt %, and from 5 to 50 wt %. In other embodiments, the aromatic compound conversion lower limit may be 1 wt %, 5 wt %, 10 wt %, 15 wt %, 20 wt %, 25 wt %, 30 wt %, 35 wt %, and 40 wt %, and the aromatic compound conversion upper limit may be 95 wt %, 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, and 20 wt % with ranges from any lower limit to any upper limit being contemplated.

In one another embodiment, the cyclic monoolefin selectivity in the hydrogenation step is from 1 to 100 wt %. Preferably, the cyclic monolefin selectivity of the hydrogenation step is from 20 to 99.9 wt %; from 25 to 99.9 wt %; from 50 to 99.5 wt %; from 60 to 99.9 wt %; from 70 to 99.9 wt %; from 80 to 99.9 wt %; from 90 to 99.9 wt %; and from 95 to 99.9 wt %. In other embodiments, the cyclic monoolefin selectivity lower limit may be 1 wt %, 5 wt %, 10 wt %, 15 wt %, 20 wt %, 25 wt %, 30 wt %, 35 wt %, 40 wt %, 45 wt % and 50 wt %; and the cyclic monoolefin selectivity upper limit may be 100 wt %, 99 wt %, 98 wt %, 97 wt %, 96 wt %, 95 wt %, 94 wt %, 93 wt %, 92 wt %, 91 wt %, 90 wt %, 85 wt %, 80 wt %, 75 wt %, 70 wt %, 65 wt %, 60 wt %, 55 wt %, 50 wt %, 45 wt %, and 40 wt % with ranges from any lower limit to any upper limit being contemplated.

The cyclic monoolefin can be supplied to the alkylation step over a wide range of values, but typically is arranged such that the molar ratio of cyclic monoolefin to benzene in the alkylation feed is between about 0.01:1 and about 100:1 as measured at the input to the contacting step, such as between about 0.1:1 and about 10:1, for example between about 0.5:1 and about 1:0.5. Similarly, although the source of hydrogen is not critical, it is generally desirable that the hydrogen is at least 99 wt % pure.

The alkylation reaction is effected in the presence of a functional catalyst comprising a molecular sieve. In one preferred embodiment, the molecular sieve comprises a composite of a molecular sieve and an inorganic oxide different from the molecular sieve. In one embodiment, the molecular sieve has an average pore size of at least $7 \times 10^{-10}$ m (7 Angstrom). In another embodiment, the molecular sieve is selected from zeolite beta, faujasite (e.g. zeolite X, zeolite Y, and zeolite USY), mordenite and a molecular sieve of the MCM-22 family. Conveniently, molecular sieve may have a X-ray diffraction pattern including d-spacing maxima at 12.4±0.25, 6.9±0.15, 3.57±0.07 and 3.42±0.07 Angstrom. In still another embodiment, the molecular sieve is selected from MCM-22, PSH-3, SSZ-25, ERB-1, ITQ-1, ITQ-2, MCM-36, MCM-49, MCM-56, UZM-8, and combinations of any two or more thereof. In one embodiment, the molecular sieve is selected from an aluminosilicate, a borosilicate, and a galosilicate and the molar ratio of the silica to the aluminum, boron or gallium in the respective molecular sieve is in the range of 2:1 to 200:1, preferably in the range of 5:1 to 100:1, and more preferably in the range from 10:1 to 50:1. In still another embodiment, the molecular sieve is selected from zeolite beta, faujasite, and mordenite. Average pore size can be obtained by nitrogen gas adsorption-desorption analysis.

In one embodiment, the molecular sieve comprises an MCM-22 family material. The term "MCM-22 family material" (or "material of the MCM-22 family" or "molecular sieve of the MCM-22 family"), as used herein, includes molecular sieves made from a building block unit cell, which unit cell has the MWW framework topology. A unit cell is a spatial arrangement of atoms which if tiled in three-dimensional space describes the crystal structure. MWW framework topology is disclosed and described in the "Atlas of Zeolite Framework Types", Fifth Edition, 2001, the entire content of which is incorporated as reference.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49; (b) MCM-56; and (c) isotypes of MCM-49 and MCM-56, such as ITQ-2.

The inorganic oxide employed in such a composite alkylation catalyst is not narrowly defined provided it is stable and inert under the conditions of the alkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985). When the catalyst system comprises a composite of the molecular sieve and the inorganic oxide that is different from the molecular sieve, these two components are conveniently present in a weight ratio in the range 90:10 to 10:90, such as 80:20 to 20:80, for example 70:30 to 30:70 or 60:40 to 40:60.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the alkylation reaction using an MCM-22 family zeolite catalyst described herein is highly selective towards mono-cycloalkyl-substituted aromatic compound, the effluent from the alkylation reaction may contain some di-cycloalkyl-substituted aromatic compound by-product. Depending on the amount of this di-cycloalkyl-substituted aromatic compound, it may be desirable to either (a) transalkylate the di-cycloalkyl-substituted aromatic compound with additional benzene or (b) dealkylate the di-cycloalkyl-substituted aromatic compound to maximize the production of the desired monoalkylated species.

In one embodiment, the cyclic monoolefin and benzene supplied to the alkylation process create an alkylation composition within the alkylation zone wherein the alkylation composition comprises at least 5 wt % of benzene and 5 wt % of cyclic monoolefin as measured at the input to the contacting step, at least 10 wt % of benzene and 5 wt % of cyclic monoolefin as measured at the input to the contacting step, at least 15 wt % of benzene and 10 wt % of cyclic monoolefin as measured at the input to the contacting step, at least 20 wt % of benzene and 10 wt % of cyclic monoolefin as measured at the input to the contacting step, at least 50 wt % of benzene and 10 wt % of cyclic monoolefin as measured at the input to the contacting step. For clarity, the cyclic monoolefin and benzene may be supplied separately to the alkylation zone wherein the cyclic monoolefin and benzene become mixed within the alkylation zone to create the alkylation composition.

In one embodiment, the effluent contains at least 5 wt % of the cycloalkyl-substituted aromatic compound, the effluent contains at least 10 wt % of the cycloalkyl-substituted aromatic compound, the effluent contains at least 15 wt % of the cycloalkyl-substituted aromatic compound, the effluent contains at least 20 wt % of the cycloalkyl-substituted aromatic compound, the effluent contains at least 25 wt % of the cycloalkyl-substituted aromatic compound, and the effluent contains at least 30 wt % of the cycloalkyl-substituted aromatic compound.

The conditions employed in the alkylation process are important in achieving the desired selectivity to mono-cycloalkyl-substituted aromatic compound and include a temperature of about 50° C. to about 350° C., about 50° C. to about 200° C., about 50° C. to about 175° C., about 50° C. to 145° C., or more preferably about 100° C. to about 145° C. The alkylation conditions may also include a pressure of from about 0 kPag to 5000 kPag (0 psig to about 725 psig), from 345 kPag to 2068 kPag (50 psig to 300 psig), and from about 690 kPag to 1380 kPag (100 psig to 200 psig). The alkylation conditions may also include a cyclic monoolefin to benzene molar ratio of from 0.01:1 to 100:1, from 0.1:1 to 100:1, from 0.1:1 to 10:1, from 0.2 to 10:1. The alkylation conditions may also include a weight hourly space velocity of benzene of about 0.1 to about 100 $hr^{-1}$, particularly about 0.1 to about 10 $hr^{-1}$.

In one embodiment, the operating temperature of the alkylation process is from 50° C. to 400° C. Preferably, the operating temperature of the alkylation process is from 50° C. to 250° C.; from 75° C. to 225° C.; from 100° C. to 200° C., from 100° C. to 145° C., and from 110° C. to 145° C., from 120° C. to 145° C., from 120° C. to 140° C., and from 125° C. to 135° C. In other embodiments, the operating temperature lower limit may be 50° C., 75° C., 100° C., 110° C., 120° C., 125° C., 130° C., 135° C., 140° C., 145° C.; and the upper limit temperature may be 500° C., 400° C., 300° C., 200° C., 190° C., 180° C., 170° C., 160° C., 150° C., 145° C., 140° C., 135° C., and 130° C. with ranges from any lower limit to any upper limit being contemplated.

Transalkylation with additional benzene is typically effected in a transalkylation reactor, separate from the alkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/di-cycloalkyl-substituted aromatic compound weight ratio about of 1:1 to about 5:1. The transalkylation reaction effluent can then be returned to the second distillation tower to recover the additional mono-cycloalkyl-substituted aromatic compound product produced in the transalkylation reaction.

Cyclohexylbenzene Oxidation

In a preferred embodiment, the cyclohexylbenzene produced by the process of the invention is further converted. Thus, in order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N''-trihydroxyisocyanuric acid.

These catalytic materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount of from 0.0001 mol % to 15 mol %, such as from 0.001 mol % to 5 mol %, of the cyclohexylbenzene.

Suitable conditions for the oxidation step include a temperature between about 70° C. and about 200° C., such as about 90° C. to about 130° C., and/or a pressure of about 50 to 10,000 kPa. Any oxygen-containing gas, preferably air, can be used as the oxidizing medium. The reaction can take place in batch reactors or continuous flow reactors.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C. and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

Catalytic Distillation

In one embodiment, the mono-cycloalkyl-substituted aromatic compound (e.g. cyclohexylbenzene) is produced using a catalyst distillation system comprising a catalyst distillation reaction column. The benzene and cyclic monoolefin (e.g. cyclohexene) may be introduced at any point in the catalyst distillation column. The mono-cycloalkyl-substituted aromatic compound has a higher boiling point than the reactants and the mono-cycloalkyl-substituted aromatic compound will exit the reaction zone as quickly as it is formed due to the nature of the catalytic distillation. Ultimately, the mono-cycloalkyl-substituted aromatic compound will exit the catalyst distillation column at the bottom portion of the column. The removal of the mono-cycloalkyl-substituted aromatic compound minimizes formation of poly-cycloalkyl-substituted aromatic compounds and decomposition of the mono-cycloalkyl-substituted aromatic compound.

At least a portion of the benzene and cyclic monoolefin will boil because of the lower boiling point than the mono-cycloalkyl-substituted aromatic compound that is being produced. In one embodiment, some of this cyclic monoolefin and benzene will be refluxed while other will exit the catalytic distillation column overhead. The boiling of the benzene and cyclohexene increases the driving force because the reactants have been removed and cannot contribute to a reverse reaction.

Alkylation conditions within the catalyst distillation column may include 0 to 500 psig (0 to 3450 kPag) and 50° C. to 500° C. The temperature will vary depending on the reactants and products and the temperature along the column will be highest at the bottom and lowest at the top.

The conditions employed in the catalytic distillation alkylation process are important in achieving the desired selectivity to cyclohexylbenzene and include a temperature of about 50° C. to about 350° C., about 50° C. to about 200° C., about 50° C. to about 175° C., about 50° C. to 145° C., or more preferably about 100° C. to about 145° C. The catalytic distillation alkylation conditions may also include a pressure of from about 0 kPag to 5000 kPag (0 psig to about 725 psig), from 345 kPag to 2068 kPag (50 psig to 300 psig), and from about 690 kPag to 1380 kPag (100 psig to 200 psig). The catalytic distillation alkylation conditions may also include a cyclic monoolefin to benzene molar ratio of from 0.01:1 to 100:1, from 0.1:1 to 100:1, from 0.1:1 to 10:1, from 0.2 to 10:1.

In one embodiment, the operating temperature of the catalytic distillation alkylation process is from 50° C. to 400° C. Preferably, the operating temperature of the catalytic distillation alkylation process is from 50° C. to 250° C.; from 75° C. to 225° C.; from 100° C. to 200° C., from 100° C. to 145° C., from 110° C. to 145° C., from 120° C. to 145° C., from 120° C. to 140° C., and from 125° C. to 135° C. In other embodiments, the operating temperature lower limit may be 50° C., 75° C., 100° C., 110° C., 120° C., 125° C., 130° C., 135° C., 140° C., 145° C.; and the upper limit temperature may be 500° C., 400° C., 300° C., 200° C., 190° C., 180° C., 170° C., 160° C., 150° C., 145° C., 140° C., 135° C., and 130° C. with ranges from any lower limit to any upper limit being contemplated.

Referring now in more detail to the preferred embodiment illustrated in FIG. 1, a catalytic distillation tower or column comprises one or more catalyst trays in a catalytic reaction zone 1 and includes an intake for the cyclic monoolefin 2 and benzene 3, just below the catalytic reaction zone 1. Unreacted benzene and any unreacted cyclohexene produced may be condensed and refluxed via reflux stream 6 back to the column and/or removed from the reactor via overhead stream 10. The mono-cycloalkyl-substituted aromatic compound and heavies (i.e. compounds with higher boiling point that the mono-cycloalkyl-substituted aromatic compound) are removed from the bottom portion of the column via bottoms stream 8. The upper portion of the column, comprising the catalytic reaction zone 1, contains an alkylation catalyst in a distillation packing. The lower portion of the column 7 is comprised of conventional counter-current distillation internal arrangements. Optionally, the benzene may be fed at other column locations, including either into or above the catalytic distillation zone 7.

An option is to include a conventional distillation zone 11 above the catalytic distillation zone, in order to keep cyclohexyl benzene out of the overhead distillate stream 10.

The following Examples are given for illustrative purposes and do not limit the scope of the invention.

EXAMPLES

Examples 1 and 2

Alkylation catalysts used in the following examples were in extrudate form. Prior to loading into a fixed bed reactor, the extrudates were cut into particles of L/D (length/diameter) of approximately one. 700 mg of catalyst was mixed with 1 gram of 40 mesh quartz chips, and the mixture was packed into a ¼" (0.64 cm) stainless steel reactor. The alkylation catalyst was pretreated by heating up to 300° C. and holding at 300° C. for 2 hours under 50 standard cubic centimeters per minute (sccm) of nitrogen gas flow. The reactor temperature was then reduced to desired temperatures such as 145° C. prior to feed introduction. A mixed feed containing 75 wt % benzene and 25 wt % of cyclohexene was delivered at 48 μl/min using an ISCO pump. The feed was vaporized prior to mixing with 10 sccm of nitrogen. The mixture was fed into a down flow reactor. The reaction was typically run at 100° C. to 145° C., and 165 psig total reactor pressure. The weight hourly space velocity (WHSV) worked out to be about 3.53 $hr^{-1}$.

The effluent from the reactor was analyzed using a GC equipped with a FID for analysis. All the hydrocarbons were analyzed and the results were normalized. Benzene conversion and cyclohexene conversion were calculated based on the following formula, respectively, wherein benzene conversion, wt %=(75 wt % benzene in effluent)/75*100 and cyclohexene conversion, wt %=(25 wt % cyclohexene in effluent)/25*100. The results of the experiments are shown in Table 1 (40 wt % MCM49/60 wt % alumina) and Table 2 (80 wt % MCM49/20 wt % alumina)

TABLE 1

| Alkylation Catalyst | Temperature, ° C. | | |
|---|---|---|---|
| 40 wt % MCM49/60 wt % alumina | 145° C. | 120° C. | 100° C. |
| Benzene conversion, wt % | 19.99 | 19.00 | 6.72 |
| Cyclohexene conversion, wt % | 99.51 | 89.41 | 47.22 |
| CHB selectivity, wt % | 73.69 | 79.91 | 51.43 |
| di-CHB selectivity, wt % | 14.61 | 8.44 | 2.99 |
| Total selectivity for CHB and di-CHB, wt % | 88.30 | 88.35 | 54.41 |

TABLE 2

| Alkylation Catalyst | Temperature, ° C. | | |
|---|---|---|---|
| 80 wt % MCM49/20 wt % alumina | 145° C. | 120° C. | 100° C. |
| Benzene conversion, wt % | 16.60 | 19.04 | 7.27 |
| Cyclohexene conversion, wt % | 99.50 | 92.64 | 50.57 |
| CHB selectivity, wt % | 71.61 | 78.72 | 53.25 |
| di-CHB selectivity, wt % | 16.68 | 10.42 | 4.34 |
| Total selectivity for CHB and di-CHB, wt % | 88.29 | 89.15 | 57.59 |

The data in both Table 1 and Table 2 show that the selectivity of cyclohexylbenzene (CHB) is unexpectedly optimum between the temperatures of 100° C. and 145° C. while the selectivity for both CHB and di-cyclohexylbenzene (di-CHB) is comparable.

Example 3

A formulated catalyst (65 wt % MCM-22/35 wt % alumina) was used for this work. The MCM-22 crystal had a SiO2/Al2O3 weight ratio around 25. The catalyst was in the form of 1/16" (0.16 cm) cylindrical extrudate. Chemical grade benzene and cyclohexene were used. Each feed was percolated over an activated alumina prior to use. The percolated feeds were mixed so the benzene/cyclohexene molar ratio was 4:1.

A 0.8 gram sample of the formulated catalyst, sized so that the length of the catalyst was equal to its diameter, was diluted with washed sand to 3 cc. The well-mixed catalyst/sand mixture was charged to a stainless steel fixed-bed micro-reactor. The reactor had a 3/8" inch (1 cm) outside diameter with a 1/8 inch (0.32 cm) thermowell in the center throughout the catalyst bed. The catalyst was dried with 100 cc/min of flowing N2 for 2 hours at 125° C. and 1 atm. After drying (with $N_2$ off now), benzene was fed into the reactor through a syringe pump at 60 cc/hour for 1 hr while the reactor pressure was increased to 300 psig (2070 kPag). Benzene rate was then reduced to 7 cc/hr (7.6 WHSV), and cyclohexene was introduced to the reactor at 2.0 cc/hr (2 WHSV). Once stabilized, the reactor temperature was increased to 130° C. Liquid products were collected in a cold product trap and analyzed offline. Various test conditions were used to evaluate catalyst performance by varying process variables.

The results are shown in Table 3. Cyclohexylbenzene (CHB) can be produced by direct alkylation of benzene with cyclohexene at the conditions described below. CHB selectivity of 86-88 wt % could be achieved with the overall $C_{18}$ product selectivity between 8-9 wt %.

TABLE 3

| | Sample # | | | | | |
|---|---|---|---|---|---|---|
| | 1 | 2 | 3 | 4 | 5 | 6 |
| Days on Stream | 0.9 | 1.9 | 2.9 | 3.9 | 4.9 | 5.9 |
| Temperature, ° C. | 130 | 130 | 150 | 150 | 150 | 150 |
| Press, kPag | 2140 | 2140 | 2140 | 2140 | 2140 | 2140 |
| Cyclohexene WHSV | 2.03 | 2.03 | 2.03 | 2.03 | 2.03 | 2.03 |
| Benzene WHSV | 7.65 | 7.65 | 7.65 | 7.65 | 7.65 | 7.65 |
| Cyclohexene Conv, % | 40.8 | 30.7 | 63.9 | 60.7 | 52.4 | 51.3 |
| Product Composition, wt % | | | | | | |
| Light hydrocarbons | 0.15 | 0.15 | 0.78 | 0.47 | 0.48 | 0.47 |
| Methyl-cyclohexane | 0.04 | 0.08 | 0.08 | 0.08 | 0.08 | 0.07 |
| Toluene | 0.04 | 0.05 | 0.03 | 0.02 | 0.04 | 0.03 |
| Cyclohexylbenzene (CHB) | 86.01 | 87.62 | 85.96 | 86.57 | 87.42 | 86.67 |
| Other $C_{12}$s | 1.40 | 1.26 | 3.97 | 4.02 | 3.68 | 4.21 |
| m-di-CHB | 5.89 | 6.09 | 5.00 | 5.03 | 4.97 | 4.97 |
| p-di-CHB | 3.36 | 2.48 | 3.50 | 3.41 | 2.95 | 3.09 |
| Other $C_{18}$s | 0.00 | 0.00 | 0.68 | 0.38 | 0.25 | 0.39 |
| Others | 3.11 | 2.27 | 0.01 | 0.02 | 0.14 | 0.09 |
| Sum | 100.0 | 100.0 | 100.0 | 100.0 | 100.0 | 100 |
| Overall $C_{18}$ Products | 9.25 | 8.57 | 9.17 | 8.82 | 8.18 | 8.45 |

In Table 3, "light hydrocarbons" means hydrocarbons having 1-5 carbon atoms (C1-C5). "Other C12s" means hydrocarbons having 12 carbon atoms, excluding cyclohexylbenzene. "m-di-CHB" means meta-dicyclohexylbenzene. "p-di-CHB" means para-dicyclohexylbenzene. "Other $C_{18}$s" means hydrocarbons having 18 carbon atoms (C18), excluding meta-dicyclohexylbenzene and para-dicyclohexylbenzene. "Others" means any other product components other than those listed above. "Overall $C_{18}$ products" means all hydrocarbons having 18 carbon atoms (C18).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing a mono-cycloalkyl-substituted aromatic compound, the process comprising contacting an alkylation composition comprising benzene and a cyclic monoolefin with an alkylation catalyst under alkylation conditions to produce an effluent containing the cycloalkyl-substituted aromatic compound, wherein the alkylation conditions comprise a temperature of from 100° C. to 145° C., a pressure of from 345 kPa, gauge to 2068 kPa, gauge, and wherein the alkylation composition has a cyclic monoolefin to benzene molar ratio of from 0.10:1 to 10:1 as measured at the input to the contacting step; and
    wherein the alkylation catalyst comprises a composite of (i) a molecular sieve selected from MCM-22, PSH-3, SSZ-25, ERB-1, ITQ-1, ITQ-2, MCM-36, MCM-49, MCM-56, UZM-8, and combinations of any two or more thereof; and (ii) an inorganic oxide different from the molecular sieve.

2. The process of claim 1, wherein the conditions comprise a temperature of from 110° C. to 145° C.

3. The process of claim 1, wherein the effluent contains at least 5 wt % of the cycloalkyl-substituted aromatic compound.

4. The process of claim 1, wherein the alkylation composition comprises at least 10 wt % of benzene and 10 wt % of cyclic monoolefin as measured at the input to the contacting step.

5. The process of claim 1, wherein the molecular sieve has an average pore size of at least $7 \times 10^{-10}$ m (7 Angstrom).

6. The process of claim 1, wherein the molecular sieve has an X-ray diffraction pattern including d-spacing maxima at 12.4±0.25, 6.9±0.15, 3.57±0.07 and 3.42±0.07 Angstrom.

7. The process of claim 1, wherein the molecular sieve is an aluminosilicate and the molar ratio of the silica to the aluminum in the molecular sieve is in the range of 2:1 to 200:1.

8. The process of claim 1, wherein the mono-cycloalkyl-substituted aromatic compound is cyclohexylbenzene and the cyclic monoolefin is cyclohexene.

9. The process of claim 1, wherein the effluent also contains dicyclohexylbenzene and at least part of the dicyclohexylbenzene is contacted with benzene under transalkylation conditions to produce further cyclohexylbenzene.

10. The process of claim 8, further comprising oxidizing at least a portion of the cyclohexylbenzene to produce cyclohexylbenzene hydroperoxide, and cleaving at least a portion of the cyclohexylbenzene hydroperoxide to produce phenol and cyclohexanone.

11. The process of claim 1, wherein the cyclic monoolefin is produced by the hydrogenation of an aromatic compound and wherein the cyclic monoolefin conversion in the hydrogenation step is from 5 wt % to 50 wt %.

* * * * *